(12) United States Patent
Oppelt et al.

(10) Patent No.: US 6,193,731 B1
(45) Date of Patent: Feb. 27, 2001

(54) LAPAROSCOPIC INSERTION AND DEPLOYMENT DEVICE

(75) Inventors: William G. Oppelt, Arroyo Grande; Greg Graham, Ventura; John Blackmore, Redwood City; Ronald F. Haynes, San Luis Obispo, all of CA (US)

(73) Assignee: FzioMed, Inc., San Luis Obispo, CA (US)

( * ) Notice: Subject to any disclaimer, the term of this patent is extended or adjusted under 35 U.S.C. 154(b) by 0 days.

(21) Appl. No.: 09/181,010

(22) Filed: Oct. 27, 1998

(51) Int. Cl.$^7$ .................................................. A61B 17/08

(52) U.S. Cl. ............................................ 606/151; 604/13

(58) Field of Search ................................ 606/151, 154, 606/190–191, 213, 1; 604/13–18

(56) References Cited

U.S. PATENT DOCUMENTS

| | | | |
|---|---|---|---|
| 5,257,973 | 11/1993 | Villasuso | 604/49 |
| 5,263,927 | 11/1993 | Shlain | 604/13 |
| 5,295,952 | 3/1994 | Pietrafitta | 604/1 |
| 5,304,187 | 4/1994 | Green et al. | 606/151 |
| 5,310,407 | 5/1994 | Casale | 604/51 |
| 5,464,403 * | 11/1995 | Kieturkaris et al. | 606/151 |
| 5,503,623 * | 4/1996 | Tilton, Jr. | 606/151 |
| 5,558,652 * | 9/1996 | Henke | 604/280 |

* cited by examiner

Primary Examiner—Michael Buiz
Assistant Examiner—Jonathan D. Goldberg
(74) Attorney, Agent, or Firm—Fliesler, Dubb, Meyer & Lovejoy

(57) ABSTRACT

A device for inserting a substantially square sheet of flexible material through a laparoscopic cannula into an abdominal cavity. The device is an elongate, generally cylindrical member having a proximal end and a distal end and a body portion therebetween. A pair of tines is rigidly affixed to the distal end of the body portion with a slot separating the tines. A handle is affixed to the proximal end of the body portion. The slot defined between the pair of tines is dimensioned to accommodate the sheet thickness therewithin. In a preferred use, the sheet of material is inserted between the tines with diagonal corners of the sheet within the slot. The free corners of the sheet are drawn together with one hand and the handle of the device is rotated to wrap the sheet around the exterior surface of the two tines. The distal end of the body portion is then inserted into a laparoscopic cannula and advanced therethrough with a twisting motion until the distal end of the device emerges from the cannula positioned within the abdominal cavity. At this point, the device is slightly withdrawn to dislodge the film from the receptacle at the base of the tines and the sheet unwinds from around the tines, effectively unfolding the sheet within the target cavity. The sheet is finally released from the slot between the tines when the device is withdrawn from the cannula; the sheet remaining within the abdominal cavity.

33 Claims, 4 Drawing Sheets

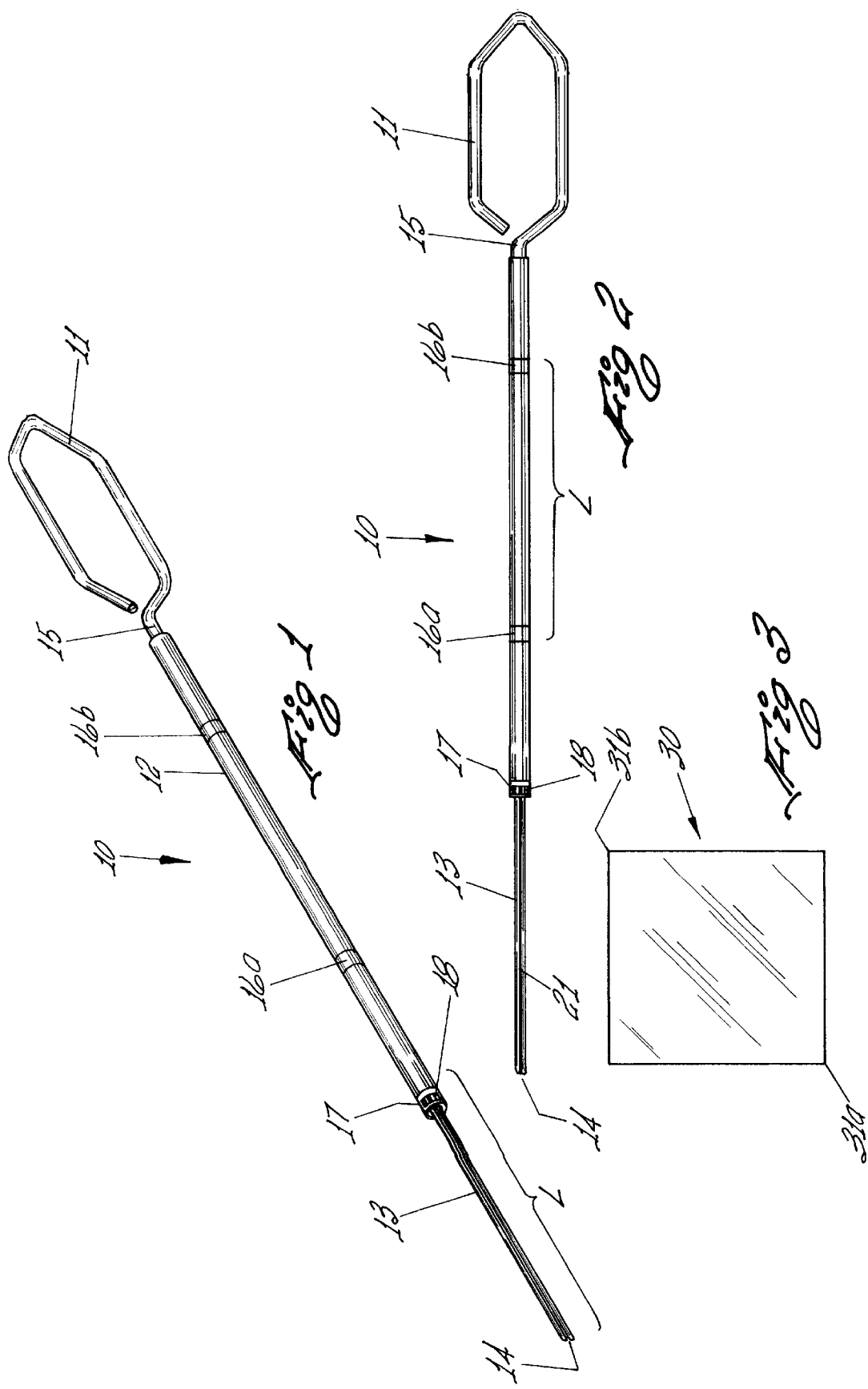

LAPAROSCOPIC INSERTION AND DEPLOYMENT DEVICE

BACKGROUND OF THE INVENTION

1. Field of the Invention

The present invention related to a device for inserting a film or sheet of bioabsorbable material into the abdominal cavity of a patient during laparoscopic surgery.

2. Prior Art

Laparoscopic surgery involves the transcutaneous placement of at least one, and usually two, three or four laparoscopic cannulas through the abdominal wall to provide a conduit into the abdomen. The cannula(s) are inserted by means of a trocar placed against the skin which, in response to pressure, provides a open pathway into abdominal cavity through which the cannula(s) may pass. One of such cannulas is employed to inflate the abdominal cavity with carbon dioxide gas to improve the field of view and accessibility to organs within the abdomen. Others are used for the insertion of specialized surgical instruments. All such cannulas are fitted with a leak-proof valve to prevent gas under pressure from leaking from within the abdominal cavity. Instruments used in laparoscopic surgery are passed through the cannulas and manipulated within the abdominal cavity. One of the cannulas houses a camera which, together with a light source, provides a means for a physician or surgeon to view the field of operation and perform a surgical procedure within the abdominal cavity.

It has been difficult in the art to insert sheets of flexible material through such cannulas for deployment within the abdominal cavity. Films or sheets of material which are particularly desirable for such insertion include adhesion barriers, bioabsorbable and biodegradable drug releasing films and the like.

The prior art has dealt with the problem of inserting sheets of material through a cannula into the abdomen in a variety of ways, some of which are set forth in U.S. Pat. No. 5,503,623 by Tilton, Jr. In particular, the Tilton Jr. patent ('623) discloses a laparoscopic device which is operable through a cannula and which employs a set of jaws to grasp a sheet, wind said sheet around said jaws, retract said jaws and sheet into a sheath, and inserting the sheath through the cannula into the abdomen then advancing the jaws and sheet through the sheath and, when the jaws and sheet are clear of the cannula, releasing the sheet. Such devices are expensive and difficult to clean. It is, therefore, desirable to provide a device which can be used in laparoscopic surgery to insert and deploy a sheet or film of flexible material into an abdominal cavity which obviates some or all of the problems associated with prior art devices.

SUMMARY OF THE INVENTION

It is a first object of this invention to provide a device for inserting and deploying a flexible sheet or film of a surgical material within the abdominal cavity of a patient undergoing laparoscopic surgery.

It is a further object of the invention to provide a method for inserting and deploying a flexible square sheet of surgical material within the abdominal cavity during laparoscopic surgery.

It is yet another object of the invention to provide a device for inserting and deploying a sheet or film of surgical material within a cavity during laparoscopic surgery which device is inexpensive to manufacture.

It is another object of the invention to provide a device for inserting and deploying a sheet or film of surgical material within a target cavity during laparoscopic surgery which is simple to use.

It is an additional object of the invention to provide a reusable device for inserting and deploying a sheet or film of surgical material within a target cavity during laparoscopic surgery which device can be more easily and thoroughly cleaned and sterilized.

The features of the invention believed to be novel are set forth with particularity in the appended claims, however, the invention itself, both as to organization and method of operation together with further objects and advantages thereof may best be understood by reference to the following description taken in conjunction with the accompanying drawings in which:

BRIEF DESCRIPTION OF THE DRAWINGS

FIG. 1 is a perspective view of a preferred embodiment of the film insertion device in accordance with the present invention.

FIG. 2 illustrates a horizontal view of the device of FIG. 1.

FIG. 3 is a top view of a sheet of film suitable for insertion and deployment within a target cavity, such as an abdominal cavity, by means of the device of FIGS. 1 and 2.

DESCRIPTION OF THE PREFERRED EMBODIMENTS

Figure 4:
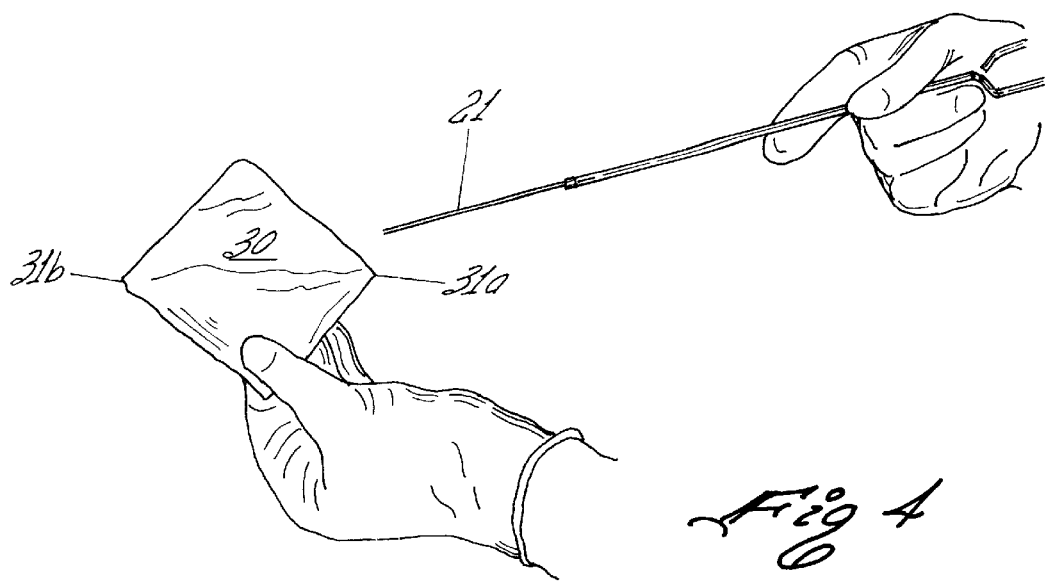
FIG. 4 is a perspective view showing the orientation of a sheet of film immediately prior to its placement within the slot defined by and between the distal tines of the device of FIGS. 1 and 2.

Turning first to FIG. 1, a film insertion device is shown in perspective view at 10. The device is generally an elongate member having a proximal end 15 affixed to a handle 11 and a distal end indicated at 14 and a body portion 12 therebetween. The handle portion 11 is designed to be grasped by and held within a hand (not shown). The body portion 12 has a pair of tines 13 projecting in an axial direction from the distal end thereof The tines 13 have a usable length L. At the proximal end of the tines 13, a cup-shaped receptacle 17 is affixed thereto. While the receptacle 17 is shown in FIGS. 1–9 as abutting the body portion 12 with the tines 13 extending distally therefrom, it should be understood that the receptacle 17 may be spaced from the body portion 12 with the tines projecting distally therefrom. The receptacle 17 has an opening 18 in the lateral portion of the cup-shaped distal end thereof which enables the receptacle 17 to be flushed of contaminating fluids such as blood. The body portion 12 of the film insertion device 10 may further include two markers 16a and 16b.

In FIG. 2, a side view of the device 10 is shown. The tines 13 have a slot 21 therebetween which slot is open on the distal end 14 and terminates proximally at the receptacle 17. If markers 16a and 16b are present on the body portion, the spacing between such markers is approximately the same as the usable length L of the tines 13.

Turning next to FIG. 3, a sheet of film is shown in top view which is adapted for transcutaneous insertion through the spin 84 (FIGS. 8 and 9) into the abdominal cavity 85 of a patient undergoing laparoscopic surgery. The sheet of film 30 has two pair of opposing diagonal corners, the first pair is shown as 31a and 31b. The distance between the opposing corners 31a and 31b is L.

The sheet of film 30 can be easily positioned in the slot 21 (FIGS. 2 & 4) between the tines 13 (FIGS. 1 & 2) of the film insertion device 10 as shown in FIGS. 4–7.

In FIG. 4, we see the sheet of film 30 being slid into the slot 21 and advanced proximally to the receptacle 17.

Figure 5:
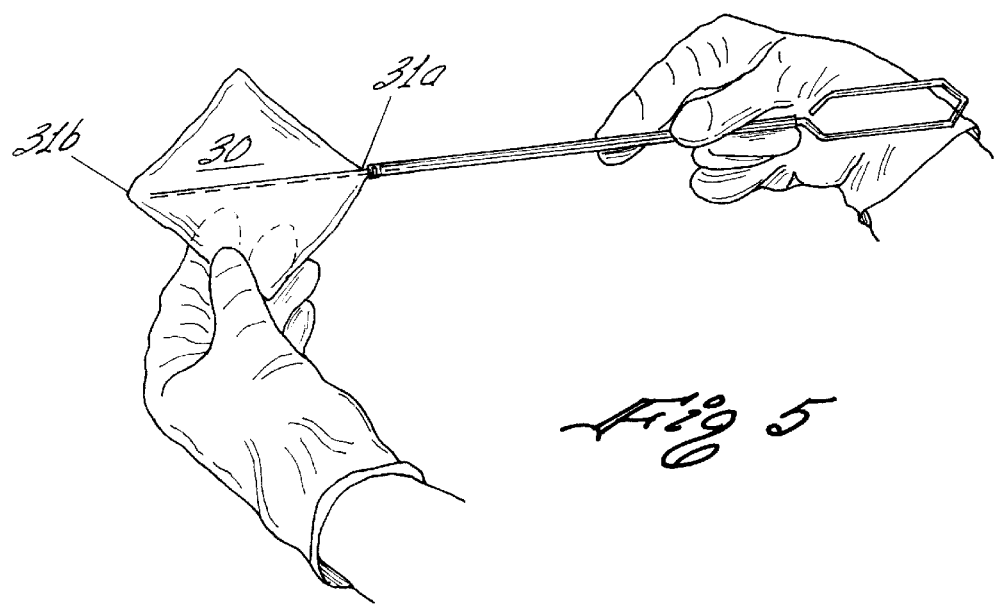
FIG. 5 shows the film in a first, open position within the slot defined by and between the distal tines of the device of FIGS. 1 and 2.

FIG. 5 shows corner 31a of the film 30 positioned within the receptacle 17.

Figure 6:
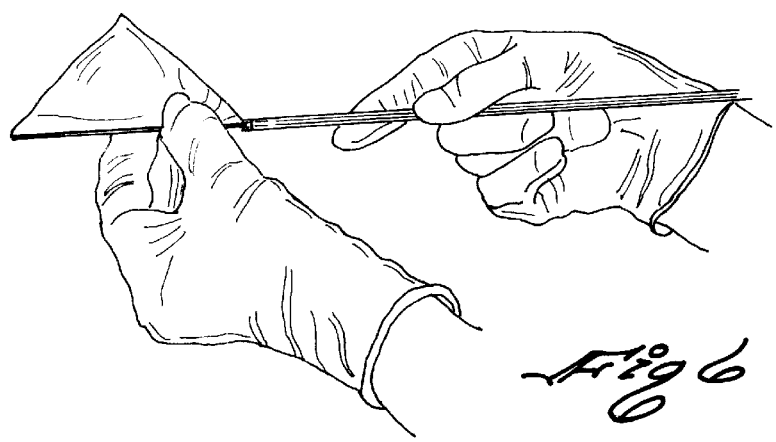
FIG. 6 is a perspective illustration of the film in a second position, namely, diagonally opposing corners of the sheet folded over one of the distal tines of the device of FIGS. 1 and 2.

FIG. 6 shows the second pair of opposing corners (not numbered) brought together into juxtaposition and held there by a free hand.

Figure 7:
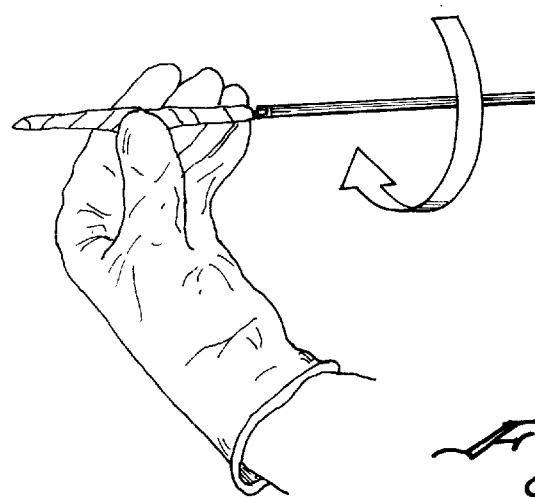
FIG. 7 shows the twisting motion which creates a third position of the sheet of film being fully twisted over both distal tines of the device of FIGS. 1 and 2.
Figure 8:
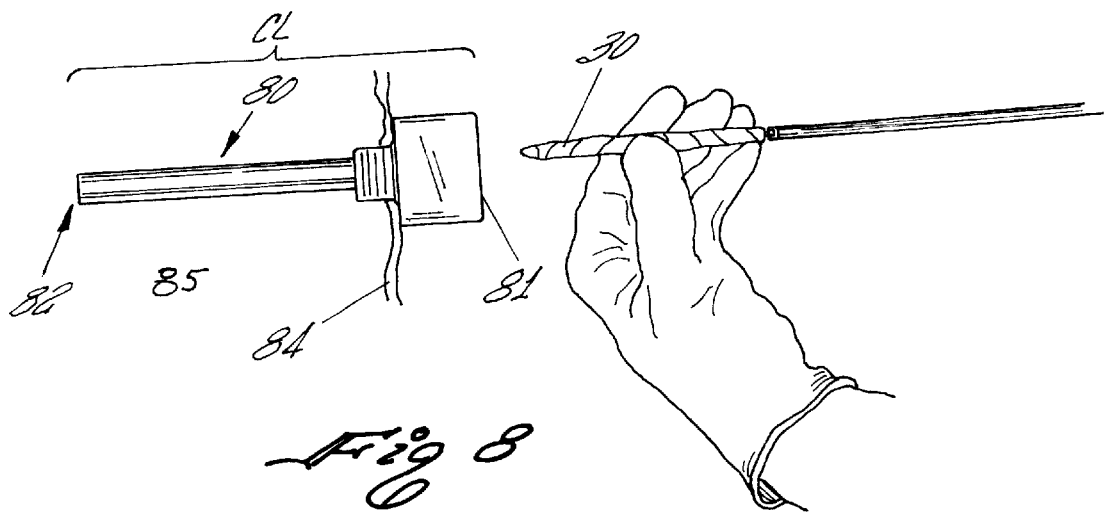
FIG. 8 is a perspective view illustrating the sheet and device of FIG. 7 with the film properly positioned immediately prior to insertion of the distal tines into the inner lumen of a laparoscopic cannula.
Figure 9:
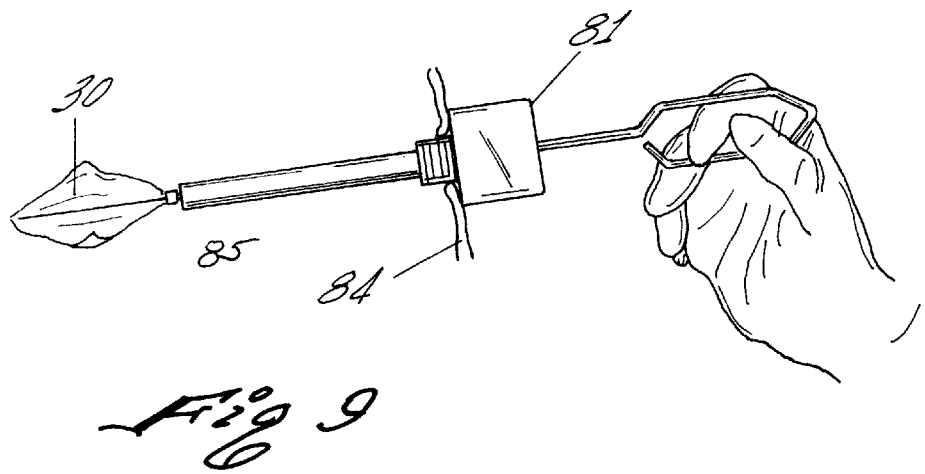
FIG. 9 is a perspective side view showing the sheet, device and cannula of FIG. 8 immediately following advancement of the device and sheet into an abdominal cavity (not shown).
Figure 10:
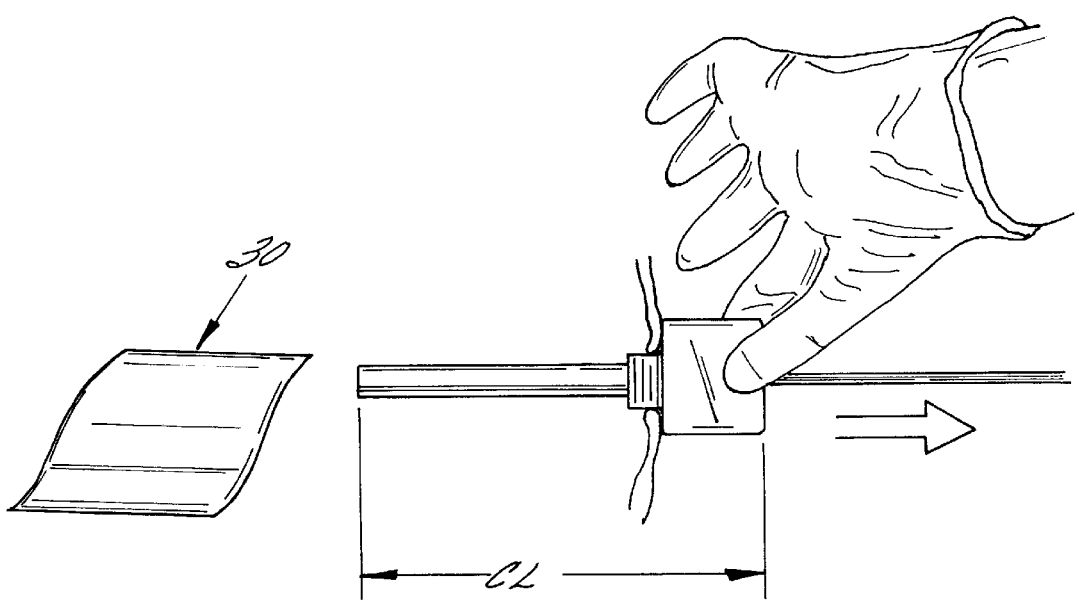
FIG. 10 is a perspective diagram illustrating deployment of the sheet of FIG. 3 within an abdominal cavity (not shown) following retraction of the device of FIGS. 1 and 2 from the laparoscopic cannula (shown in FIGS. 8 and 9).

Turning now to FIG. 7, twisting of the film insertion device's handle portion 11 results in wrapping the film around the tines 13 of the film insertion device 10. While holding the wrapped film sheeting in the wrapped position around the tines 13, the distal end 14 of the insertion device 10 is inserted into the proximal end of a laparoscopic cannula 80 which cannula 80 provides an access conduit between the skin 84 of a patient and the abdominal cavity 85. The proximal end 81 of the cannula is fitted with a gas leak-proof insertion valve (not shown) which prevents gas within the abdomen from escaping. The distal end of the insertion device 10 is inserted through the gas leak-proof valve and the device is twisted or screwed into the cannula until the distal end of the insertion device exits the cannula 80. The sheet of film is then further advanced through the cannula until the distal end of the insertion device projects therefrom and the film is completely beyond the distal end 82 of the cannula 80 (as shown in FIG. 9) and the device is retracted thereby dislodging the corner 31a of the film 30 from within the confines of the receptacle 17. At this point, the sheet of film 30 unrolls or is grasped by another instrument such that when the insertion device is retracted from the cannula the film slides from the slot, leaving it deployed within the abdominal cavity as shown in FIG. 10.

The markers on the body portions 16a and 16b are positioned on the body portion as follows. The distance from the marker 16a to the distal end 14 is equal to the length of the cannula used CL. The distance between the distal market 16a and the proximal marker 16b is equal to L, the diagonal length between the first pair of opposing corners, 31a and 31b (which equals the slot length). Thus, in operation, it is possible to insert the film insertion device into the lumen of the cannula and when the marker 16a is flush with the proximal end 81 of the cannula, the film is beginning to emerge from the distal end of the cannula. Further advancement of the insertion device through the cannula until the marker 16b is flush with the proximal end of the cannula provides visual evidence that the slot, tines and film have all emerged from the distal end of the laparoscopic cannula and is disposed within the abdominal cavity. At this point, the film unrolls and the insertion device is withdrawn.

While particular embodiments of the present invention have been illustrated and described, it would be obvious to those skilled in the art that various other changes and modifications can be made without departing from the spirit and scope of the invention.

While the present invention may be used for inserting a film or sheet through an access tube such as an endoscope projecting into any target cavity within a patient's body, for simplification in disclosing the present invention, the abdominal cavity was referred to herein. Such referral is exemplary and not intended to limit the scope of the invention, but to provide an example of the subject device and its method for use. It is therefore intended to cover in the appended claims all such changes and modifications that are within the scope of this invention.

What we claim is:

1. A device for inserting a film into a cavity of a patient, the device comprising:

(a) an elongate cylindrical body portion dimensioned to slidably fit within an axial conduit of a laparoscopic cannula having a conduit length, the body portion having a proximal end, a distal end having a receptacle adapted to receive a portion of said film and a body length therebetween wherein said body length is greater than the conduit length;

(b) a handle rigidly affixed to said proximal end of said body portion; and (c) two tines, each having a proximal end rigidly affixed to said receptacle, a distal end said tines defining a slot having a slot length and a slot width separating the two tines, wherein the slot width is adapted to be greater than or equal to the sheet thickness.

2. The device of claim 1 wherein said polymeric sheet is square and has a diagonal dimension, and wherein said slot has a length substantially equal to said diagonal dimension of said polymeric sheet.

3. The device of claim 1 further comprising a receptacle affixed to said distal end of said body portion and wherein said slot extends between said receptacle and said distal end of said tines.

4. The device of claim 2 further comprising a receptacle affixed to said distal end of said body portion and wherein said slot extends between said receptacle and said distal end of said tines.

5. The device of claim 1 wherein said conduit of said cannula has a conduit length and wherein said body portion has a distal marker thereon positioned a first distance from said distal end of said tines, and wherein said first distance and said conduit length are substantially equal.

6. The device of claim 2 wherein said conduit of said cannula has a conduit length and wherein said body portion has a distal marker thereon positioned a first distance from said distal end of said tines, and wherein said first distance and said conduit length are substantially equal.

7. The device of claim 3 wherein said conduit of said cannula has a conduit length and wherein said body portion has a distal marker thereon positioned a first distance from said distal end of said tines, and wherein said first distance and said conduit length are substantially equal.

8. The device of claim 4 wherein said conduit of said cannula has a conduit length and wherein said body portion has a distal marker thereon positioned a first distance from said distal end of said tines, and wherein said first distance and said conduit length are substantially equal.

9. The device of claim 5 further comprising a proximal marker on said body portion positioned proximal to said distal marker at a second distance from said distal marker wherein said second distance is equal to said slot length.

10. The device of claim 6 further comprising a proximal marker on said body portion positioned proximal to said distal marker at a second distance from said distal marker wherein said second distance is equal to said slot length.

11. The device of claim 7 further comprising a proximal marker on said body portion positioned proximal to said distal marker at a second distance from said distal marker wherein said second distance is equal to said slot length.

12. The device of claim 8 further comprising a proximal marker on said body portion positioned proximal to said distal marker at a second distance from said distal marker wherein said second distance is equal to said slot length.

13. A method for inserting a flat square sheet of a film through a conduit within a laparoscopic cannula which projects into a target cavity of a patient comprising the steps of:
    (a) presenting a device comprising:
        (1) an elongate body portion dimensioned to fit within an axial conduit of a laparoscopic cannula, the body portion having a proximal end, a distal end having a receptacle adapted to receive a portion of said sheet, and a body length therebetween, wherein said body length is greater than the conduit length;
        (2) a handle rigidly affixed to said proximal end of said body portion;
        (3) two tines, each having a proximal end rigidly affixed to said receptacle and a distal end, said tines defining a slot having a slot length and a slot width separating the two tines; then
    (b) inserting said sheet of a film into said slot so that two diagonally opposed corners of said sheet of film are positioned within the slot between the two tines; then
    (c) folding the sheet to bring the remaining two diagonally opposed corners of the sheet in juxtaposition; then
    (d) twisting said handle of said device to wrap said sheet around said tines; then
    (e) inserting said distal end of said device having said sheet of film wrapped around said tines into said proximal end of said conduit in said cannula; then
    (f) advancing said device through said conduit in said cannula until said sheet exits said distal end of said conduit in said cannula and unwraps; then
    (g) retracting said device from said cannula, said sheet remaining is said cavity.

14. A device for inserting a sheet of material into a body cavity, comprising:
    (a) an elongate body having a first end with a handle and a second end with a receptacle adapted to receive a portion of said sheet and having a distal end; and
    (b) means for holding the sheet, said holding means associated with and extending beyond the distal end of said receptacle.

15. A device for inserting a sheet of material into a body cavity, comprising:
    (a) an elongate body having a first end with a handle and a second end with a receptacle adapted to receive a portion of said sheet and having a distal end; and
    (b) a sheet holder associated with and extending beyond the distal end of said receptacle.

16. The device of claim 15, wherein said receptacle has a concave shape.

17. The device of claim 15, wherein said second end has a lateral wall and the receptacle has an opening on a lateral wall.

18. A method for delivering a sheet of material into a body cavity of a patient, comprising the steps of:
    (a) providing a device having an elongate body having a receptacle adapted to receive a portion of said sheet and having a distal end and a sheet holder associated with and extending beyond the distal end of said receptacle;
    (b) engaging a sheet of material with said receptacle and sheet holder;
    (c) inserting said device into said body cavity; and
    (d) permitting said sheet to disengage from said receptacle and sheet holder.

19. The method of claim 18, wherein step (a) includes wrapping said sheet of material around said sheet holder.

20. The method of claim 18 further comprising after step (b), the step of wrapping said sheet around said tines.

21. A method for inserting a sheet of a film through a conduit within a laparoscopic cannula which projects into a target cavity of a patient comprising the steps of:
    (a) presenting a device comprising:
        (1) an elongate body portion dimensioned to fit within an axial conduit of a laparoscopic cannula, the body portion having a proximal end a distal end having a receptacle adapted to receive a portion of said sheet and a body length therebetween, wherein said body length is greater than the conduit length;
        (2) a handle rigidly affixed to said proximal end of said body portion;
        (3) two tines, each having a proximal end rigidly affixed to said receptacle and a distal end, said tines defining a slot having a slot length and a slot width separating the two tines; then
    (b) inserting said sheet of a film into said slot; then
    (c) twisting said handle of said device to wrap said sheet around said tines; then
    (d) inserting said distal end of said device having said sheet of film wrapped around said tines into said proximal end of said conduit in said cannula; then
    (e) advancing said device through said conduit in said cannula until said sheet exits said distal end of said conduit in said cannula and unwraps; then
    (f) permitting said sheet to disengage from said device.

22. A device for inserting a flexible sheet having a sheet thickness through a conduit within a cannula and into a target body cavity, said cannula having a proximal end and a distal end, said distal end being disposed within said cavity, said device comprising:
    an elongate member dimensioned to fit within said conduit of said cannula, said elongate member having a proximal end, a distal end having a receptacle adapted to receive a portion of said sheet and a body portion therebetween, a pair of tines, each tine having a proximal end rigidly affixed to said distal end of said body portion and extending axially therefrom, each tine having a distal end, said tines having a length and defining a slot therebetween, said slot being adapted to accommodate a sheet and a handle portion extending from said distal end of said elongate member.

23. A device for inserting a sheet of material into a body cavity, comprising:
    (a) an elongate body having a first end with a handle and a second end with a receptacle adapted to receive a portion of said sheet and having a distal end; and (b) two tines defining a slot therebetween, each of said tines having a proximal end and a distal end, said proximal ends extending from within said receptacle, and said distal ends of said tines extending beyond said distal end of said receptacle.

24. The device of claim 23, wherein said receptacle has a lateral wall having an opening.

25. The device of claim 23, wherein said slot extends into said receptacle.

26. The device of claim 23, wherein said receptacle has a back wall, and wherein said slot extends to said back wall.

27. The device of claim 23, wherein said slot is adapted to accommodate a width of a sheet.

28. The device of claim 23, including a marker positioned at a first distance from said distal ends of said tines.

29. The device of claim 23, including a plurality of markers, each marker being positioned at a defined distance from said distal ends of said tines.

30. The device of claim 23, further comprising a cannula adapted to be placed in a body cavity, said cannula having a lumen having an interior diameter sufficiently large to permit passage of said elongate body through said lumen.

31. The device of claim 23, wherein said distal ends of said tines are joined together.

32. The device of claim 23, wherein said tines are rigid.

33. The device of claim 23, wherein said tines are rigidly affixed to said elongate body.

* * * * *